(12) United States Patent
Keenan et al.

(10) Patent No.: US 7,186,866 B1
(45) Date of Patent: Mar. 6, 2007

(54) PROCESS FOR RECOVERY OF CUMENE HYDROPEROXIDE DECOMPOSITION PRODUCTS BY DISTILLATION

(75) Inventors: Scott R. Keenan, Marlton, NJ (US); Amber R. Harach, Hockessin, DE (US); James G. Skipworth, Franklin Furnace, OH (US)

(73) Assignee: Sunoco, Inc. (R&M), Philadelphia, PA (US)

( * ) Notice: Subject to any disclaimer, the term of this patent is extended or adjusted under 35 U.S.C. 154(b) by 0 days.

(21) Appl. No.: 11/273,411

(22) Filed: Nov. 14, 2005

(51) Int. Cl.
*C07C 49/20* (2006.01)
*C07C 37/68* (2006.01)

(52) U.S. Cl. ...................... 568/385; 568/385
(58) Field of Classification Search ............... 568/385, 568/754
See application file for complete search history.

(56) References Cited

U.S. PATENT DOCUMENTS

| | | |
|---|---|---|
| 4,251,325 A | 2/1981 | Marsh et al. |
| 4,340,447 A | 7/1982 | Laverick et al. |
| 5,414,154 A | 5/1995 | Jenczewski et al. |
| 5,998,677 A | 12/1999 | Yasaka et al. |
| 6,388,144 B1 | 5/2002 | Wijesekera et al. |
| 6,620,980 B1 | 9/2003 | Emblidge et al. |
| 2002/0068840 A1* | 6/2002 | Weber et al. ............ 568/385 |

* cited by examiner

Primary Examiner—Joseph K. McKane
(74) Attorney, Agent, or Firm—Robert A. Koons, Jr.; Matthew P. McWilliams; Drinker Biddle & Reath LLP

(57) ABSTRACT

Products from the decomposition of cumene hydroperoxide (CHP) are recovered by distillation. The majority of the undesirable by-product acetol (hydroxyacetone) is removed from the phenol stream by distillation wherein the majority of the acetol is carried with an overheads stream comprising acetone, cumene and alphamethylstyrene (AMS). Acetol is subsequently separated from acetone by distillation wherein acetone is taken as an overheads stream and acetol remains with a bottoms stream comprising cumene, AMS and phenol. The acetol, along with residual phenol, is extracted from the cumene and AMS by counter-current washing with an aqueous alkali metal hydroxide. The phenol stream is then distilled to separate phenol from cumene, alphamethylstyrene and higher boiling compounds. The phenol, containing only a small amount of acetol, can then be treated to remove methylbenzofuran by treatment with an acidic resin or solid superacid catalyst without formation of significant amounts of additional methylbenzofuran.

15 Claims, 1 Drawing Sheet

PROCESS FOR RECOVERY OF CUMENE HYDROPEROXIDE DECOMPOSITION PRODUCTS BY DISTILLATION

FIELD OF THE INVENTION

The present invention relates to the production of phenol, acetone and alphamethylstyrene by the decomposition of cumene hydroperoxide. More particularly, the present invention relates to a method for the recovery of products from the decomposition of cumene hydroperoxide by distillation.

BACKGROUND OF THE INVENTION

The oxidation of cumene to cumene hydroperoxide (CHP) and its subsequent acid catalyzed decomposition results in three products that have value either as products in and of themselves or for recycle. These are phenol, acetone and alphamethylstyrene (AMS). In addition, cumene is generally present in the CHP fed to the process, either as residual from the cumene oxidation step or added as a diluent. This cumene is recovered for recycle to the oxidation step.

In addition to these several products that have value, the oxidation of cumene to CHP and its subsequent decomposition results in a multitude of impurities that must be removed from the product phenol and acetone, as well as the AMS and cumene. Two impurities of particular importance in phenol production are acetol (hydroxyacetone) and methylbenzofurans. Both of these impurities lead to unacceptable color on further processing of phenol, such as in the production of bisphenol A.

Previous patents, such as U.S. Pat. No. 5,414,154 and U.S. Pat. No. 6,388,144, both of which are incorporated herein by reference in their entirety, have disclosed methods for removal of methylbenzofurans from phenol by thermal treatment in the presence of an acidic resin or solid superacid catalyst by converting methylbenzofurans to products boiling higher than phenol and subsequently distilling the phenol away from these products. Both of the above patents further disclose the necessity of removing acetol from the phenol stream prior to the thermal treatment to avoid the production of additional methylbenzofurans by condensation of the acetol with phenol. A typical method for removing acetol disclosed in the above patents involves treatment of the phenol stream with an amine. Such treatments, while effective, are costly in that they require an additional raw material, amine. Further, the presence of the amines in the effluent streams sent for burning results in an increase in $NO_x$ emissions.

Other processes have dealt with the problem of acetol by means of a distillation step designed to separate phenol and acetol. Such a process is described in U.S. Pat. No. 4,251,325. In the process described therein, phenol and heavier boiling products are separated from an overhead stream comprising acetone, water and products lighter than acetone. The resulting phenol stream, containing 5 to 15 percent by weight of a combination of cumene and AMS is fed to a mid-point of a distillation column. Conditions in the column are maintained such that the bottoms product of the distillation is a phenol stream containing less than 30 ppm of acetol. While effective, this method is energy intensive.

U.S. Pat. No. 4,340,447 describes a process wherein acetol is carried forward to an acetone purification column in concentrations of up to 4000 ppm. Vaporized acetone containing acetol is fed to the acetone purification column. A caustic material is fed to the column, at a point above where the acetone vapor is fed, to condense acetol and aldehydes to heavier boiling compounds. Purified acetone is removed as a side stream at a point between the acetone vapor feed and the caustic feed point. An overhead stream of less pure acetone is recycled to the column. Again, while this method is effective in producing pure acetone, the presence of significant amounts of acetol results in the fouling of the distillation column with polymerization products.

Therefore, there remains a need for an energy efficient method to remove acetol and methylbenzofurans from phenol. Such a method would not make use of expensive reagents such as amines to remove acetol, and would avoid the production of significant amounts of additional methylbenzofurans by condensation of acetol with phenol. Such a method would also limit distillation column fouling.

SUMMARY OF THE INVENTION

The current invention provides a process for recovering products from the decomposition of cumene hydroperoxide, the process comprising sequential distillation steps. In a first step a crude product stream from the decomposition of cumene hydroperoxide is fed to a first distillation column, optionally with addition of water prior to the column. The crude product stream is distilled to obtain a first overheads stream comprising acetone, cumene, alphamethylstyrene, acetol and 1 percent by weight or less of phenol, and a first bottoms stream comprising phenol, the bottoms stream containing methylbenzofuran, 0.5 percent by weight or less of alphamethylstyrene, 50 ppm by weight or less of acetol and essentially no cumene.

The first overheads stream is fed to a second distillation column, and distilled to obtain a second overheads stream comprising acetone, cumene and alphamethylstyrene, and a second bottoms stream comprising cumene, alphamethylstyrene and essentially all of the acetol and phenol from the first overheads stream.

The second overheads stream is subsequently fed to a third distillation column comprising a reaction zone and a separation zone, and distilled in the presence of an aqueous alkali metal hydroxide. A slip stream comprising acetone, aldehydes and products lighter than acetone is removed from the top of the separation zone and recycled to the reaction zone. A third overheads stream comprising acetone and a third bottoms stream comprising cumene and alphamethylstyrene are thereby obtained The second bottoms stream is fed to a scrubber, wherein the second bottoms stream is contacted with an aqueous alkali metal hydroxide stream to produce an aqueous effluent stream containing solubilized phenol, alkali metal phenate and acetol, and an organic effluent stream comprising cumene and alphamethylstyrene, wherein the organic effluent stream is essentially free of phenol and acetol. Optionally, the third bottoms stream is combined with the second bottoms stream and the combined streams are fed to the scrubber.

The first bottoms stream is directed to a fourth distillation column, and distilled to obtain a fourth overheads stream comprising phenol and essentially all of the alphamethylstyrene and cumene contained in the first bottoms stream. A fourth bottoms stream comprising phenol and products heavier than phenol is produced, as well as a first side stream comprising phenol, methylbenzofuran and acetol.

The first side stream is fed to an acidic resin bed at a temperature of about 100° C. or higher at a rate of about 2 bed volumes per hour or less to convert methylbenzofuran and acetol to products boiling higher than phenol. The first side stream thus treated is fed to a fifth distillation column, and distilled to obtain a fifth overheads stream comprising phenol and products lighter than phenol. A fifth bottoms stream comprising phenol and products heavier than phenol is produced, as well as a second side stream comprising a high purity phenol, preferably containing less than 50 ppm by weight of impurities.

DETAILED DESCRIPTION OF THE INVENTION

Figure 1:
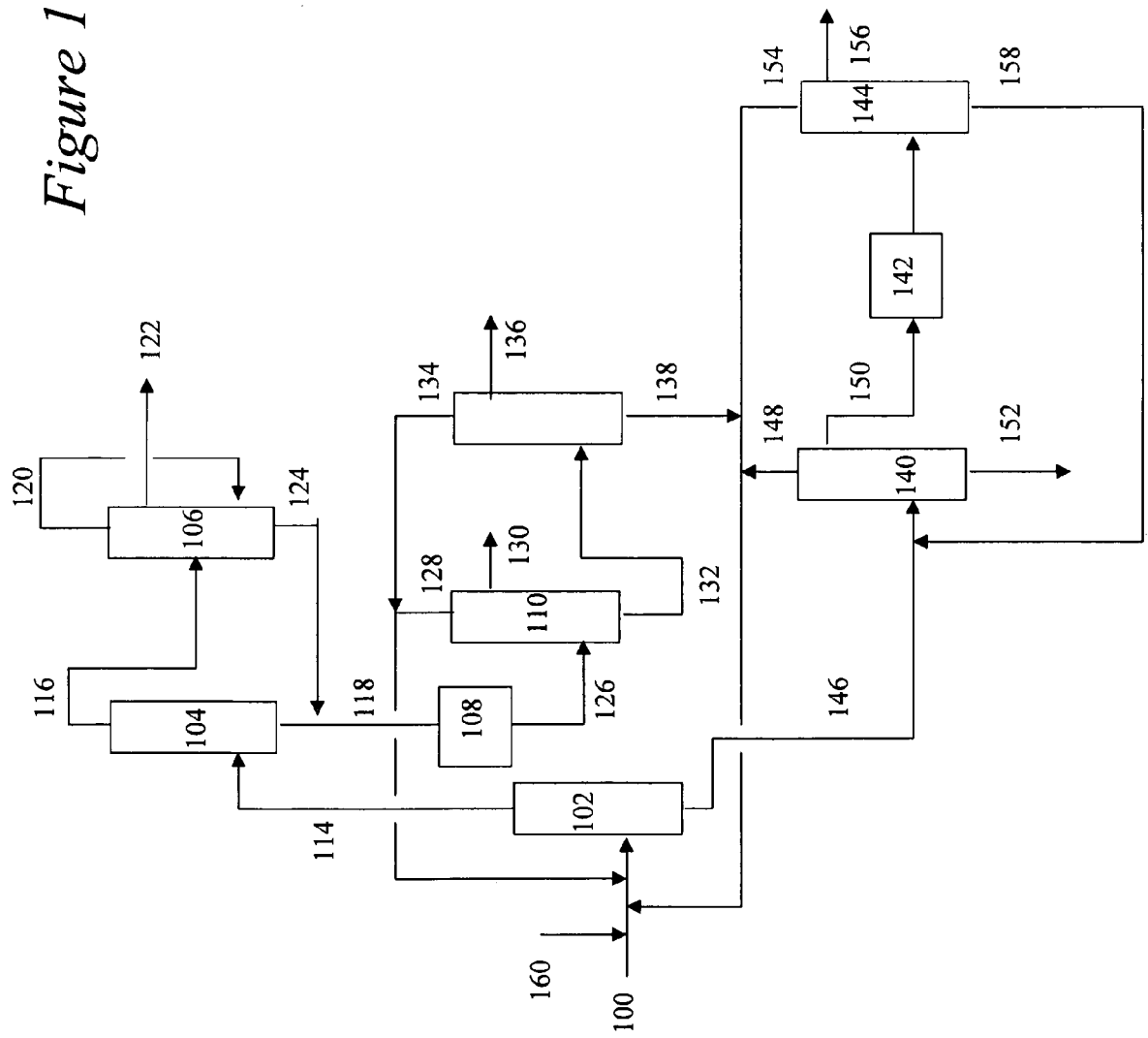
FIG. 1. Illustrates an exemplary process flow according to the present invention.

The present invention is a process for recovering the various products from the decomposition of cumene hydroperoxide (CHP). The present invention avoids the problems of prior art processes by removing the majority of the acetol from the phenol stream with the overheads from a first distillation step comprising acetone, cumene and AMS, but then further separating the acetol from the acetone in a second distillation step prior to exposure to an aqueous alkali metal hydroxide in the acetone refining column. Essentially all of the acetol remains with the bottoms stream from the second distillation step. This second bottoms stream comprises cumene and AMS. Once separated from the acetone stream, the acetol is subsequently removed from the cumene and AMS bottoms by extraction with an aqueous alkali metal hydroxide. This step also removes any residual phenol that may have been entrained in the overheads stream from the first distillation step. The cumene and AMS can then be separated or sent to a hydrogenation unit prior to recycle to the cumene oxidation step in the phenol process. The process according to the current invention therefore effectively removes the majority of the acetol from both the phenol and acetone streams without necessitating the use of expensive amines, which result in undesirable $NO_x$ emissions, or incurring the costs associated with process shut-downs to clear column fouling.

An exemplary embodiment of the invention will now be described with reference to FIG. 1. It should be noted that FIG. 1 and references thereto are for illustrative purposes only and are not intended to limit the invention.

Referring to FIG. 1, a crude product stream 100 from the decomposition of cumene hydroperoxide is fed to a first distillation column 102. Optionally, a small amount of water 160 is added to the crude product stream 100 prior to distillation column 102. The crude product stream is generally neutralized to a pH of from about 2.0 to about 4.0 prior to distillation. A first overheads stream 114 comprising acetone, cumene, alphamethylstyrene, acetol and phenol is produced in the first distillation column 102. According to the invention, the first overheads stream 114 contains the majority of the acetone, cumene, alphamethylstyrene and acetol from the crude product stream 100. The phenol content of the first overheads stream 114 is typically from about 0.1 to about 1 percent by weight, and is preferably less than 1 percent by weight. Also produced is a first bottoms stream 146, which comprises phenol and methylbenzofuran. The first bottoms stream 146 contains the majority of the phenol and methylbenzofuran from the crude product stream 100 and preferably contains less than 0.5 weight percent of AMS, less than 50 ppm of acetol and essentially no cumene.

As used herein, "essentially no" as it applies to the concentration of a particular component means that the concentration is reduced to an extremely low level. Those skilled in the art of distillation recognize that in many cases where components of a mixture are separated by distillation it is often difficult to obtain a complete separation of components that are structurally similar, interact with each other and/or have close boiling points. As a result, a bottoms stream from a distillation may contain a small fraction of a component, the majority of which was separated as an overheads stream in the distillation. Therefore, in the context of the present invention, while it is preferred that the first bottom stream contain no cumene, it is recognized that it may contain some residual cumene, say about 0.05 percent or less, but still be essentially free of cumene.

Still referring to FIG. 1, the first overheads stream 114 is fed to a second distillation column 104. In the distillation column 104, the first overheads stream 114 is separated into a second overheads stream 116 comprising acetone, cumene and AMS and a second bottoms stream 118 comprising cumene and AMS. The second overheads stream 116 preferably contains 11 percent by weight or less of cumene and less than 0.5 weight percent of AMS. More preferably the second overheads stream 116 contains from 1 to 5 weight percent of cumene and less than 0.2 weight percent of AMS. Most preferably, the second overheads stream 116 contains 1 to 2 weight percent of cumene and less than 0.2 weight percent of AMS. While lower concentrations of cumene are preferred, it is necessary to carry some cumene with the acetone stream to the third distillation step to affect the separation of acetone from other products. The second bottoms stream 118, which comprises most of the cumene and AMS, contains essentially all of the acetol from the first overheads stream 114, and preferably contains essentially all of the phenol from the first overheads stream 114.

Again, the term "essentially all" as used herein means that a fraction of the acetol and phenol may be carried overhead with the second overheads stream 116. Again, it will be recognized by those skilled in the art of distillation that in many cases it will not be possible to obtain a complete separation of two components by distillation. However, it is expected that the concentration of these compounds in the second overheads stream 116 will be on the order of 10 ppm or less of acetol and 5 ppm or less of phenol.

The second bottoms stream 118 is directed to a scrubber system 108 where it is contacted with an aqueous alkali metal hydroxide to extract phenol and acetol. The phenol is extracted as an alkali metal phenate, preferably sodium phenate. Such an extraction process was previously described in U.S. Pat. No. 6,620,980, which is incorporated herein by reference in its entirety. Preferably, the second bottoms stream 118 is contacted with the alkali metal hydroxide in countercurrent flow. More preferably, the scrubber system is a multistage scrubber system such as that described in U.S. Pat. No. 6,620,980. In a particularly preferred embodiment of the invention, the scrubber is operated such that in addition to alkali metal phenate, some phenol is extracted into the aqueous stream as free phenol. Most preferably, the ratio of free phenol to alkali metal phenate extracted into the aqueous stream is at least 0.5:1. The resulting aqueous stream, not shown, is then sent to a phenol recovery unit where phenol is sprung from the aqueous stream by addition of an acid. The resulting cumene/AMS stream 126 may then be sent for recovery of cumene and AMS. In the exemplary embodiment shown in FIG. 1, the cumene is separated from AMS in distillation column 110 and recycled to oxidation via stream 130. AMS is then recovered as product stream 136 from distillation column 112. It will be recognized that AMS may be recovered as a product for sale or hydrogenated back to cumene for recycle to oxidation. Further, it will be recognized that cumene and AMS may not be separated and that a combined cumene/AMS stream may be sent to a hydrogenation unit prior to recycle to oxidation.

The second overheads stream 116 is then directed to an acetone refining column 106, which comprises a reaction zone and a separation zone. An alkali metal hydroxide added to the reaction zone of the refining column 106 causes condensation of aldehyde impurities present in the acetone, which are then separated from acetone. A slipstream 120 comprising acetone, aldehydes and products lighter than acetone is removed from the top of the refining column 106 and recycled to the reaction zone. Purified product acetone is removed as a third overheads stream 122. As stated previously the carryover of some cumene and or AMS with the second overheads stream 116 is necessary to affect separation of acetone from impurities in the refining column 106. This cumene and/or AMS is removed in a third bottoms stream 124. Optionally, the third bottoms stream 124 may be combined with the second bottoms stream 118 and the combined streams may be sent to the scrubber 108 as illustrated in FIG. 1. Alternatively, the third bottoms stream 124 may be sent directly to a hydrogenation unit prior to recycle to oxidation.

Still referring to FIG. 1, the first bottoms stream 146 from the first column 102 is sent to a fourth distillation column 140. In the fourth column 140 the first bottoms stream 146 is separated into an a fourth overheads stream 148 comprising phenol, a fourth bottoms stream 152 comprising phenol and products heavier than phenol, and a first side stream 150 comprising phenol, methylbenzofurans and acetol. Preferably, the fourth overheads stream 148 contains essentially all of the cumene and AMS contained in the first bottoms stream. As shown in the exemplary FIG. 1, the fourth overheads stream may be recycled to the crude product stream 100.

The first side stream 150 is directed to a bed 142 containing an acidic catalyst, acidic resin or solid superacid catalyst, for thermal treatment. Previous U.S. Pat. No. 5,414,154 and U.S. Pat. No. 6,388,144 describe this thermal treatment in detail. The thermal treatment is conducted at a temperature above 80° C., preferably above 100° C. The flow rate of the first side stream through the bed is preferably 1 bed volumes per hour or less. In the bed 142 methylbenzofurans and acetol are converted into products boiling higher than phenol that are separable from phenol by distillation. Because the majority of the acetol in the crude phenol stream 100 is removed with the first overheads stream 114 the formation of additional methylbenzofuran during the treatment is minimal.

The first side stream 150 thus treated is then passed to a fifth distillation column 144 wherein it is separated into a fifth overheads stream 154 comprising phenol and products lighter than phenol, a fifth bottoms stream 158 comprising phenol and products heavier than phenol, and a second side stream 156 comprising high purity phenol. Preferably the second side stream contains less than 50 ppm weight of total impurities.

The fourth and fifth overheads streams 148 and 154 are preferably recycled to the crude stream 100 as indicated in FIG. 1. The fifth bottoms stream 158 is preferably recycled to the feed of the fourth distillation column 140. The fourth bottoms stream 152 may be sent directly to a boiler for steam generation, or may be sent to a separate phenol recovery column, the residue of which may be sent to the boiler.

The process of the current invention has therefore been described in general terms without reference to specific conditions for each distillation step. The distillation conditions used for each step, such as temperature and pressure will be determined by such factors as the dimensions of the distillation column used and the number of trays in the column. The full scope of the invention will be apparent from the appended claims.

What is claimed is:

1. A process for recovering products from the decomposition of cumene hydroperoxide, the process comprising the steps of:
   a. feeding a crude product stream from the decomposition of cumene hydroperoxide to a first distillation column, and distilling the crude product stream to obtain a first overheads stream comprising acetone, cumene, alphamethylstyrene, acetol and 1 percent by weight or less of phenol, and a first bottoms stream comprising phenol, the first bottoms stream containing methylbenzofuran, 0.5 percent by weight or less of alphamethylstyrene, 50 ppm by weight or less of acetol and essentially no cumene;
   b. feeding the first overheads stream to a second distillation column, and distilling the first overheads stream to obtain a second overheads stream comprising acetone, cumene and alphamethylstyrene, and a second bottoms stream comprising cumene, alphamethylstyrene and essentially all of the acetol and phenol from the first overheads stream;
   c. feeding the second overheads stream to a third distillation column comprising a reaction zone and a separation zone, and distilling the second overheads stream in the presence of aqueous caustic, wherein a slip stream comprising acetone and products lighter than acetone is removed from the top of the separation zone and recycled to the reaction zone, to obtain a third overheads stream comprising acetone and a third bottoms stream comprising cumene and alphamethylstyrene; and
   d. feeding the second bottoms stream to a scrubber, wherein the second bottoms stream is contacted with an aqueous alkali metal hydroxide stream in countercurrent flow to produce an aqueous effluent stream containing solubilized phenol, alkali metal phenate and acetol, and an organic effluent stream comprising cumene and alphamethylstyrene, wherein the organic effluent stream is essentially free of phenol and acetol.

2. The process of claim 1, further comprising;
   a. feeding the first bottoms stream to a fourth distillation column, and distilling the first bottoms stream to obtain a fourth overheads stream comprising phenol and essentially all of the alphamethylstyrene and cumene contained in the first bottoms stream, a fourth bottoms stream comprising phenol and products heavier than phenol, and a first side stream comprising phenol, methylbenzofuran and acetol;
   b. feeding the first side stream to a bed containing an acidic resin or solid superacid catalyst at a temperature of about 100° C. or higher at a rate of about 2 bed volumes per hour or less to convert methylbenzofuran and acetol to products boiling higher than phenol;
   c. feeding the first side stream thus treated to a fifth distillation column, and distilling the first side stream to obtain a fifth overheads stream comprising phenol and products lighter than phenol, a fifth bottoms stream comprising phenol and products heavier than phenol, and a second side stream comprising a high purity phenol.

3. The process according to claim 1, wherein the ratio of phenol to alkali metal phenate in the aqueous effluent stream is 0.5:1 or higher.

4. The process according to claim 1, wherein the organic effluent stream is sent to a hydrogenation step prior to being recycled to a cumene oxidation step.

5. The process according to claim 1, wherein the organic effluent stream is sent to a distillation step to separate alphamethylstyrene from cumene, and the cumene is recycled to a cumene oxidation step.

6. The process according to claim 2, wherein the fourth and fifth overheads streams are recycled back to the crude product stream.

7. The process according to claim 2, wherein the first side stream is fed to a bed containing an acidic resin or solid superacid catalyst at a temperature of about 120° to about 130° C.

8. The process according to claim 2, wherein the first side stream is fed to a bed containing an acidic resin or solid superacid catalyst at a rate of about 0.5 to 1 bed volume per hour.

9. The process according to claim 1, wherein the second overheads stream contains up to 11 weight percent cumene and less than 0.5 weight percent alphamethylstyrene.

10. The process according to claim 9, wherein the second overheads stream contains from 1 to 5 weight percent cumene.

11. The process according to claim 10, wherein the second overheads stream contains 1 to 2 weight percent cumene and less than 0.2 weight percent alphamethylstyrene.

12. The process according to claim 1, wherein the third bottoms stream is combined with the second bottoms stream and the combined second and third bottoms streams are fed to the scrubber.

13. The process according to claim 12, wherein the third bottoms stream contains less than 0.1 weight percent of acetone.

14. The process according to claim 1, further comprising adding water to the crude product stream prior to the first distillation column.

15. The process according to claim 2, wherein the high purity phenol contains less than 50 ppm by weight of impurities.

* * * * *